(12) United States Patent
Epperly

(10) Patent No.: US 9,987,062 B2
(45) Date of Patent: Jun. 5, 2018

(54) VARIABLE ANGLE BONE PLATE

(71) Applicant: ADVANCED ORTHOPAEDIC SOLUTIONS, INC., Torrance, CA (US)

(72) Inventor: Scott Epperly, Redondo Beach, CA (US)

(73) Assignee: Advanced Orthopaedic Solutions, Inc., Torrance, CA (US)

( * ) Notice: Subject to any disclaimer, the term of this patent is extended or adjusted under 35 U.S.C. 154(b) by 406 days.

(21) Appl. No.: 14/667,390

(22) Filed: Mar. 24, 2015

(65) Prior Publication Data

US 2016/0278826 A1  Sep. 29, 2016

(51) Int. Cl.
*A61B 17/80* (2006.01)
*A61B 17/86* (2006.01)

(52) U.S. Cl.
CPC ...... *A61B 17/8057* (2013.01); *A61B 17/8605* (2013.01)

(58) Field of Classification Search
CPC .................. A61B 17/8057; A61B 17/8605
USPC ........ 606/287, 289, 291, 305, 308, 315, 316
See application file for complete search history.

(56) References Cited

U.S. PATENT DOCUMENTS

| | | | |
|---|---|---|---|
| 6,306,140 B1 * | 10/2001 | Siddiqui | A61B 17/863 606/315 |
| 6,955,677 B2 | 10/2005 | Dahners | |
| 6,974,461 B1 | 12/2005 | Wolter | |
| 7,637,928 B2 | 12/2009 | Fernandez | |
| 8,273,109 B2 * | 9/2012 | Jackson | A61B 17/7032 606/273 |
| 8,337,535 B2 * | 12/2012 | White | A61B 17/8057 606/289 |
| 8,574,268 B2 | 11/2013 | Chan et al. | |
| 8,758,346 B2 | 6/2014 | Koay et al. | |
| 9,103,367 B2 * | 8/2015 | Arnett | F16B 39/28 |
| 9,314,284 B2 * | 4/2016 | Chan | A61B 17/1728 |
| 2006/0009770 A1 | 1/2006 | Speirs et al. | |
| 2009/0143824 A1 | 6/2009 | Austin et al. | |
| 2012/0143193 A1 | 6/2012 | Hulliger | |
| 2012/0323284 A1 | 12/2012 | Baker et al. | |

* cited by examiner

*Primary Examiner* — Pedro Philogene
*Assistant Examiner* — David C Comstock
(74) *Attorney, Agent, or Firm* — Burgess Law Office, PLLC

(57) ABSTRACT

A bone fixation member used to promote healing of a fracture. The fixation member having an upper surface, a lower surface, and an aperture extending between the upper surface and the lower surface. The aperture including a plurality of upper protrusions and a plurality of lower protrusions. The upper protrusions spaced longitudinally from the lower protrusions wherein the lower protrusions are out of phase with the upper protrusions. In a further example, the upper protrusions are spaced circumferentially in a common plane and the lower protrusions are spaced circumferentially in a common plane. The common plane of the upper protrusions spaced from the common plane of the lower protrusions along a longitudinal axis of the aperture with the aperture lacking protrusions between the plane of upper protrusions and plane of lower protrusions.

20 Claims, 7 Drawing Sheets

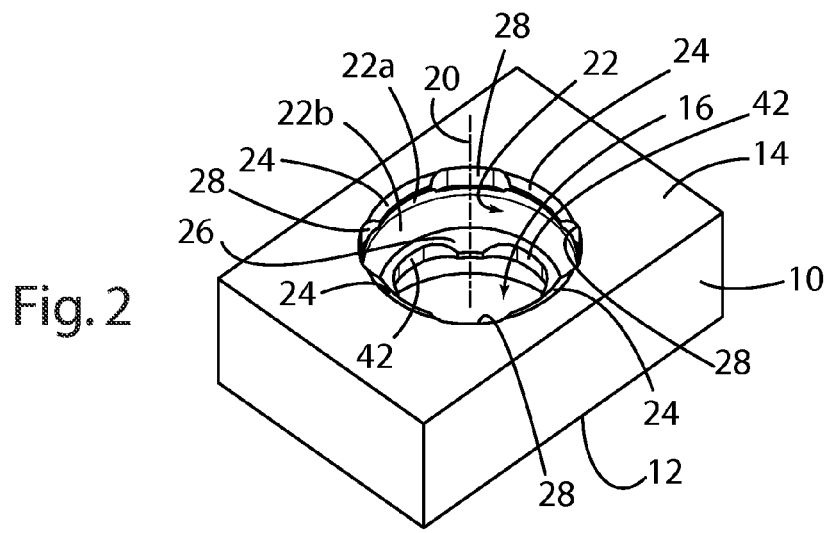
Fig. 2
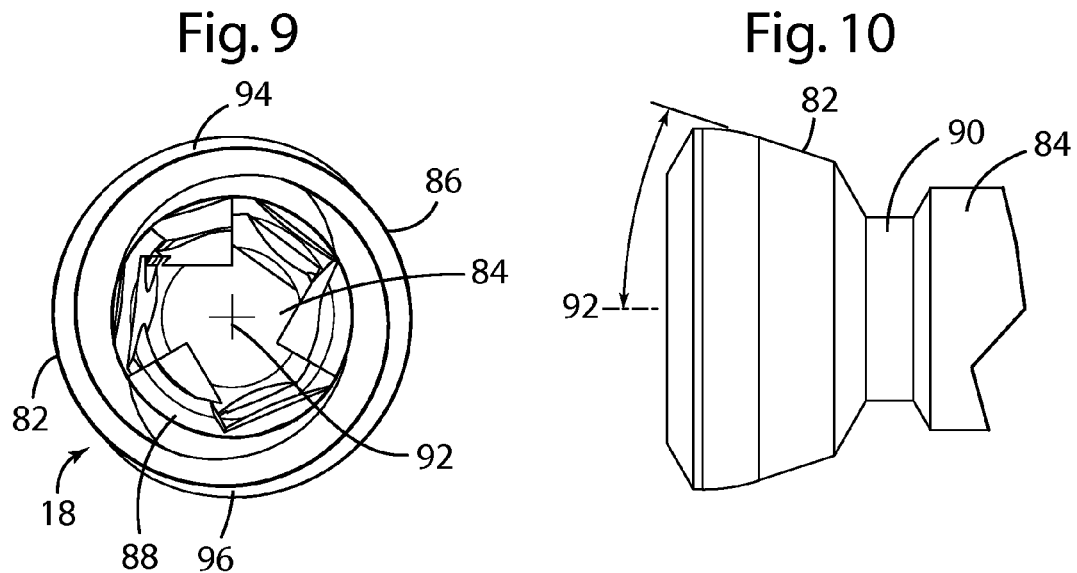
Fig. 9
Fig. 10

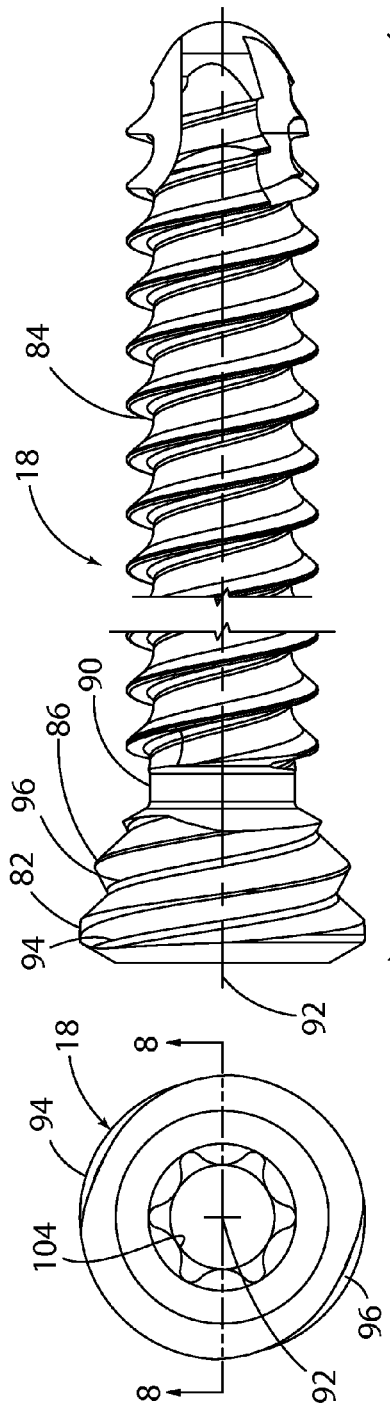
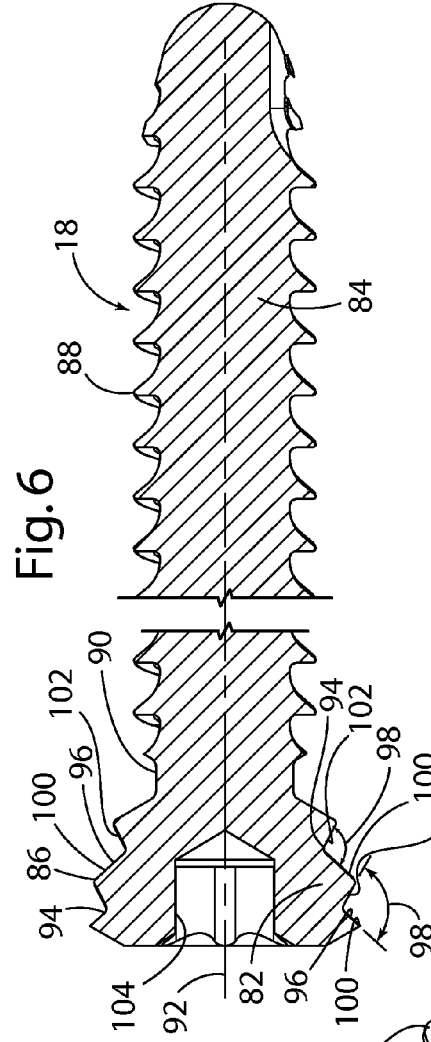
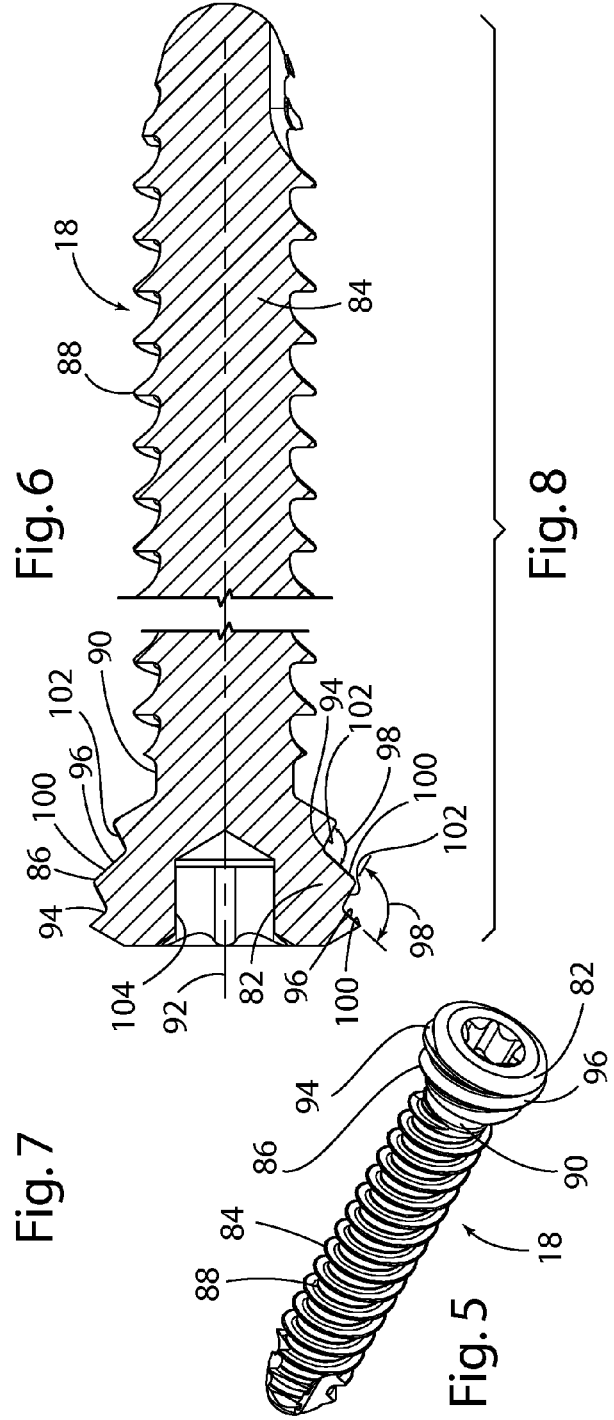

VARIABLE ANGLE BONE PLATE

CROSS-REFERENCE TO RELATED APPLICATIONS

Not Applicable

BACKGROUND OF THE INVENTION

1. Field of the Invention

The present invention relates generally to an apparatus for stabilizing bone fractures; more specifically, a bone plate capable of receiving a fixation element at an angle.

2. Description of Related Art

Bone plates are one type of fixation instrument used to promote healing of a bone fracture. The plates are typically rigid members that stabilize the site of a bone fracture by holding broken pieces of bone together. One or more fixation elements, for example bone screws, extend through openings in the bone plate and are threaded into the bone. The plate helps to properly align and immobilize the bone and aid in the healing process Bone plates may be provided with threaded holes that receive either locking or non-locking fixation elements. In addition, the bone plate may have a plurality of non-threaded holes. In some instances, depending upon bone fragmentation and fracture, insertion of the fixation element at different angles between the bone plate and a fastener enables the surgeon to reach different areas of bone or capture random fragments in various positions.

The features and advantages of the disclosure will be set forth in the description, which follows, and in part will be apparent from the description, or may be learned by the practice of the disclosure without undue experimentation. The features and advantages of the disclosure may be realized and obtained by means of the combinations particularly pointed out in the appended claims.

SUMMARY OF THE INVENTION

A bone fixation member used to promote healing of a fracture. The fixation member having an upper surface, a lower surface, and an aperture extending between the upper surface and the lower surface. The aperture including a plurality of upper protrusions and a plurality of lower protrusions. The upper protrusions spaced longitudinally from the lower protrusions wherein the lower protrusions are out of phase with the upper protrusions.

In a further exemplary embodiment, the upper protrusions are spaced circumferentially in a common plane and the lower protrusions are spaced circumferentially in a common plane. The common plane of the upper protrusions spaced from the common plane of the lower protrusions along the longitudinal axis of the aperture. The aperture lacks protrusions between the plane of upper protrusions and plane of lower protrusions.

Further areas of applicability of the disclosed embodiment will become apparent from the detailed description provided. It should be understood that the detailed description and specific examples, while indicating the preferred embodiment of the invention, are intended for illustration only and are not intended to limit the scope thereof.

BRIEF DESCRIPTION OF THE DRAWINGS

The present invention will become more fully understood from the detailed description and the accompanying drawings, wherein:

FIG. 2 is a partial perspective view of a bone plate having an aperture capable of receiving a fixation element at variable angles with respect to the centerline of the aperture according to an exemplary embodiment of the invention.

FIG. 5 is a perspective view of a fixation element for use with the aperture of FIG. 2.

FIG. 6 is a side view of the fixation element of FIG. 5.

FIG. 7 is an end view of the fixation element of FIG. 5 from the head portion thereof.

FIG. 8 is a cross-sectional view of the fixation element taken along lines 8-8 of FIG. 7.

FIG. 9 is an end view of the fixation element of FIG. 5 from the shank portion thereof.

FIG. 10 is a partial side view of the head portion of the fixation element of FIG. 5 before threading.

DETAILED DESCRIPTION OF THE PREFERRED EMBODIMENTS

Figure 1A:
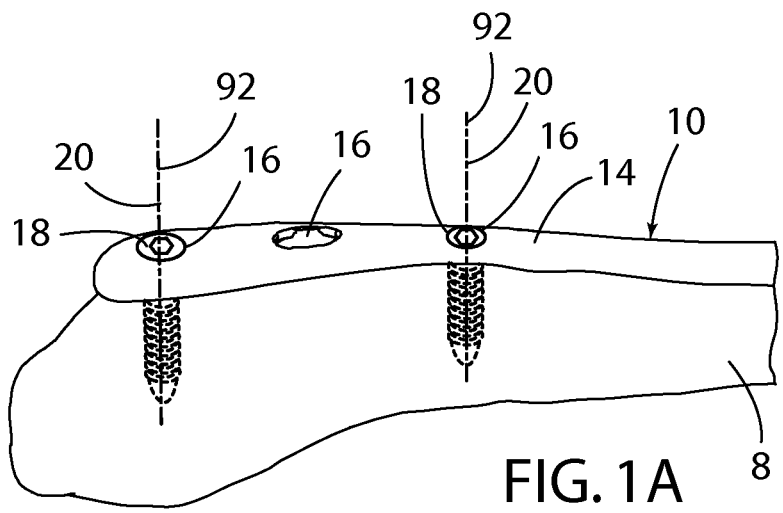
FIGS. 1A-1C illustrate perspective views of a bone fixation system according to an exemplary embodiment wherein a fixation element extends through an aperture in a bone plate and is received in the bone at various angles.

The following description of the preferred embodiment(s) is merely exemplary in nature and is not intended to limit the claims, preferred embodiment, its application, or uses.

For the purposes of promoting an understanding of these principles in accordance with the disclosure, reference will now be made to the embodiments illustrated in the drawings and specific language will describe the same. It will be understood that no limitation of the disclosure is intended. Any alterations and further modifications of the inventive features illustrated, and any additional applications of the principles of the disclosure as illustrated, which would normally occur to one skilled in the art having possession of this disclosure, are to be considered within the scope of the disclosure claimed.

Before the present apparatus and methods for treating a bone fracture are disclosed and described, it is to be understood this disclosure is not limited to the particular configurations, process steps, and materials disclosed herein as such configurations, process steps, and materials may vary somewhat. It is also to be understood that the terminology employed is used to describe particular embodiments only and is not intended to be limiting since the scope of the present disclosure will be limited only by the appended claims and equivalents thereof.

Figure 1B:
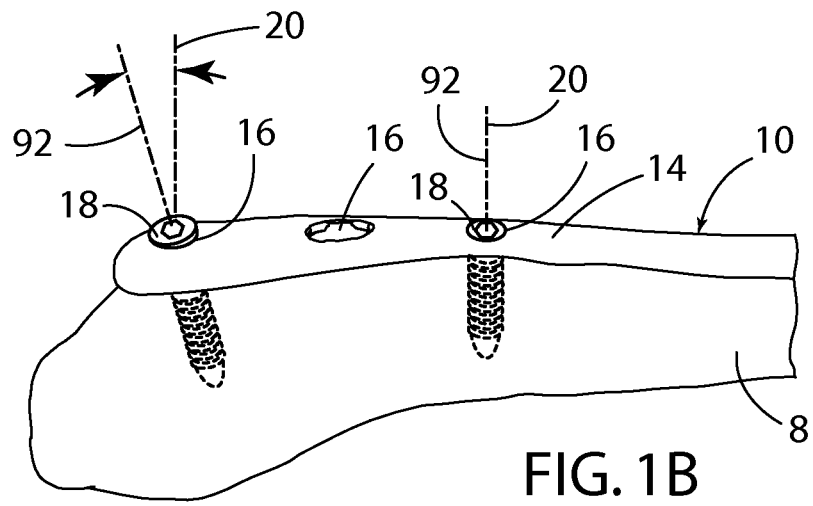
Figure 1C:
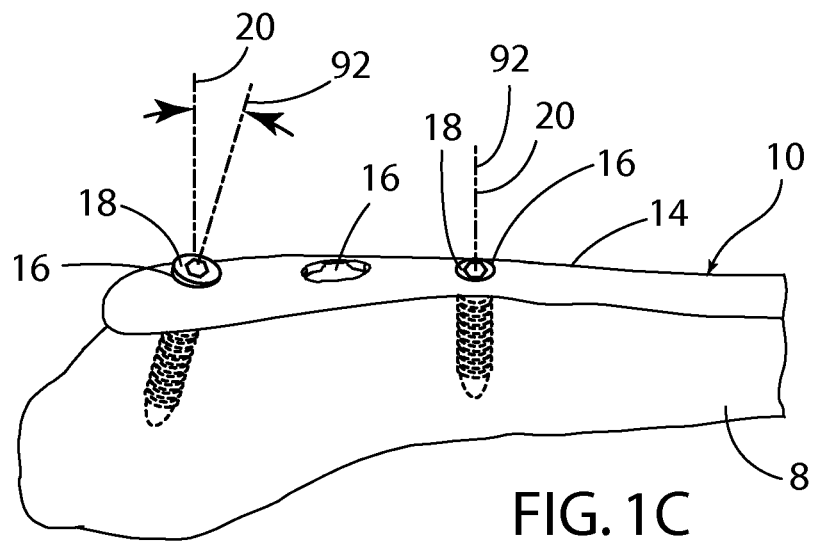

FIGS. 1A-1C illustrate a bone fixation system, according to an exemplary embodiment used with a bone 8. The bone fixation system, illustrated as a bone plate 10, includes a lower surface 12 and an upper surface 14. The lower surface 12 being the surface closer to, facing toward, and at least partially contacting the bone 8. The upper surface 14 being the surface farther from and facing away from the bone 8. The bone plate 10 including a plurality of apertures 16 extending between the lower surface 12 and the upper surface 14. The apertures 16 are intended to receive fixation elements or fasteners 18, which may include bone screws and/or the like. As set forth more fully below, and understood by a person of ordinary skill in the art, the aperture 16 receives the bone fixation element or fastener 18 at an angle relative to a central or longitudinal axis 20 of the aperture 16. Positioning and securing the fastener 18 in the aperture 16 of the bone plate 10 at various angles enables the surgeon to reach different areas of bone or capture random fragments in various positions.

FIG. 1A illustrates the fixation element or fastener 18 all positioned such that the longitudinal axis 92 of the fastener 18 coincides with the longitudinal axis 20 of the aperture 16. Typically, the longitudinal axis 20 of the aperture 16 is perpendicular to the lower surface 12 of the bone plate 10. However, the longitudinal axis 20 of the aperture 16 may also vary with respect to the bone plate 10. The longitudinal axis 20 aperture 16 according to the exemplary embodiment may also be varied with respect to a longitudinal axis or lower surface 12 of the bone plate 10 and still take advantage of the greater range of insertion angle of the fastener 18 provided by the aperture 16 as set forth.

FIGS. 1B and 1C illustrate a fastener 18 inserted into the bone 8 through the aperture 16 according to the exemplary embodiment. As illustrated the fastener 18 may be offset approximately 15° on either side the longitudinal axis 20 of the aperture 16 resulting in approximately 30° of angular variation for placement of the fastener 18.

Figure 3:
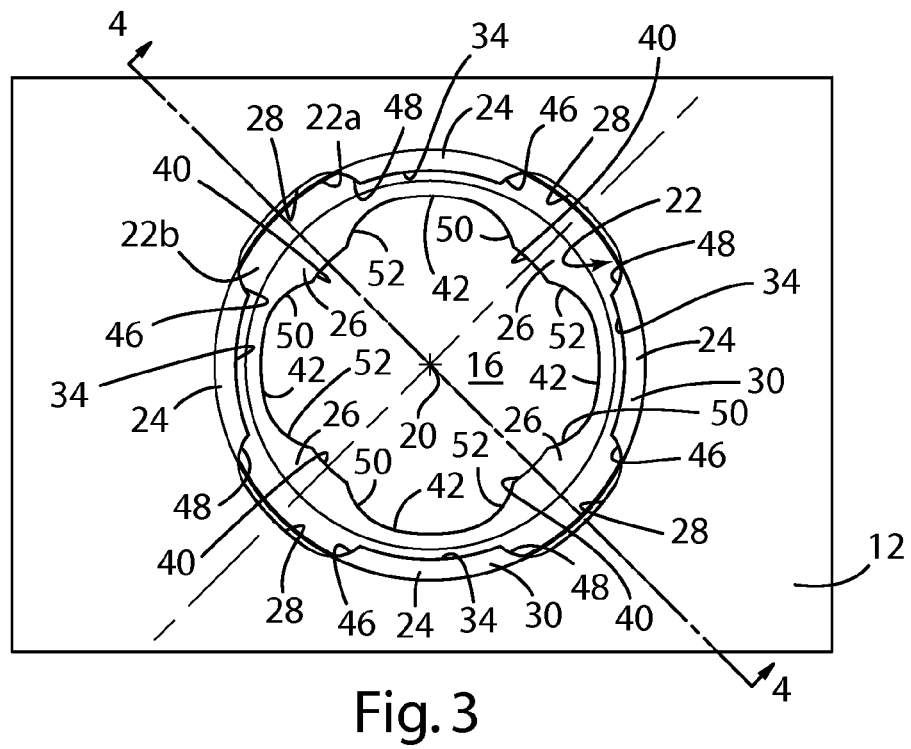
FIG. 3 is a top view of the aperture of FIG. 2.
Figure 4:
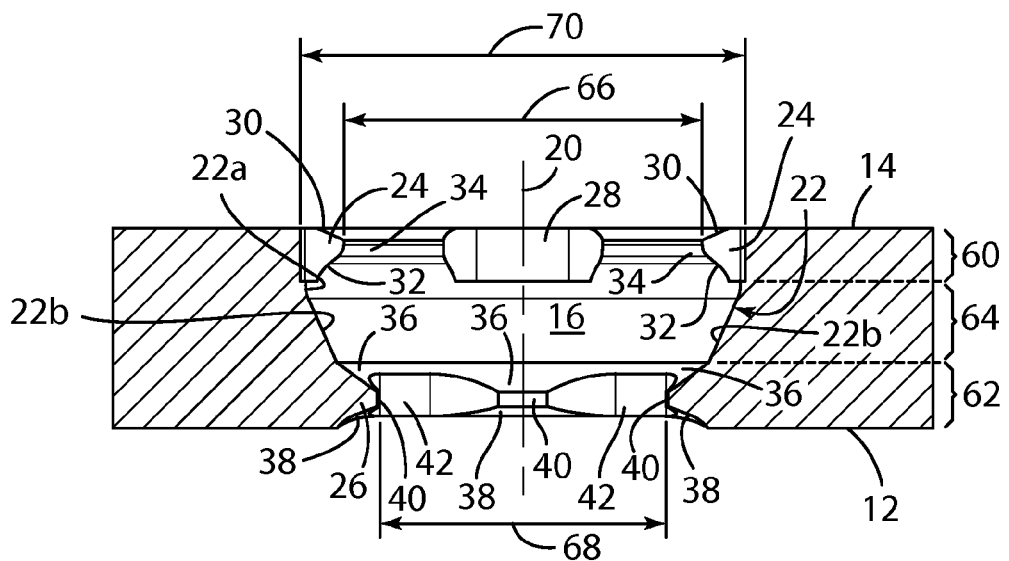
FIG. 4 is a cross-sectional view of the bone plate and aperture taken along lines 4-4 of FIG. 3.

As illustrated in FIGS. 2-4 the aperture 16 has an inner surface 22. The inner surface 22 is generally a surface of revolution about the longitudinal axis 20 of the aperture 16 and may include multiple sections having different configurations; for example, as illustrated one portion 22a of the inner surface 22 may be cylindrical while a second portion 22b of the inner surface 22 may be conical.

The inner surface 22 includes a plurality of upper protrusions 24 extending radially inwardly from the inner surface 22. The inner surface 22 further includes a plurality of lower protrusions 26 extending radially inward from the inner surface 22. As used the term upper when used with the term protrusion means those protrusions located closest to the upper surface 14 and the term lower means those protrusions located closest to the lower surface 12.

The upper protrusions 24 arranged circumferentially on the inner surface 22. As illustrated in FIG. 4, when viewed in cross-section the upper protrusions have a generally trapezoidal shaped with inwardly tapered flanks 30, 32 terminating at the crest or end 34 of the upper protrusion 24. Other configurations may also be used, for example, the protrusions may have square, round, circular, or triangular shapes. In the disclosed example, the upper protrusions 24 are all located in a common plane with gaps 28 between individual upper protrusions 24.

The sides 46, 48 of the upper protrusions 24 have a generally arcuate shape and form a gradual transition from the crest or end 34 of the upper protrusion and adjacent gaps 28. In the present example, the sides 46, 48 include a predetermined radius forming a concave junction between the upper protrusions 24 and the gaps 28.

In the present example, the crest or end 34 of the upper protrusion 24 curves circumferentially in the plane of the upper protrusion 24. Depending upon the circumferential length of the crest or end 34 of the upper protrusion 24 and the number of upper protrusions 24, the radius of curvature may change or vary, including a straight line or chord extending between the respective sides 46, 48 of the upper protrusion 24.

The lower protrusions 26 arranged circumferentially on the inner surface 22. As illustrated in FIG. 4, when viewed in cross-section the lower protrusions 26 have a generally trapezoidal shaped with inwardly tapered flanks 36, 38 terminating at the crest or end 40 of the lower protrusion 26. Other configurations may also be used, for example, the protrusions may have square, round, circular, or triangular shapes. In the disclosed example, the lower protrusions 26 are all located in a common plane with gaps 42 between individual lower protrusions 26.

The sides 50, 52 of the lower protrusions 26 have a generally arcuate shape and form a gradual transition from the crest or end 40 of the lower protrusion 26 and adjacent gaps 42. In the present example, the sides 50, 52 include a predetermined radius forming a concave junction between the lower protrusions 26 and the gaps 42.

In the present example, the crest or end 40 of the lower protrusion 26 curves circumferentially in the plane of the lower protrusion 26. Depending upon the circumferential length of the crest or end 40 of the lower protrusion 26 and the number of lower protrusions 26, the radius of curvature may change or vary, including a straight line or chord extending between the respective sides 50, 52 of the lower protrusion 26.

As illustrated FIGS. 2-4, the upper protrusions 24 are out of phase with the lower protrusions 26. As used the terms out of phase means that the upper protrusions 24 and lower protrusions 26 are offset. For example, when viewed along the longitudinal axis 20 the upper protrusions 24 and lower protrusions 26 are not circumferentially aligned; that is, when viewed in the direction of the longitudinal axis 20 the upper protrusions 24 are not located directly above the lower protrusions 26. Instead, as illustrated in the disclosed example, the upper protrusions 24 are above the lower gaps 42 between respective lower protrusions 26 and the lower protrusions 26 are below the upper gaps 28 extending between respective upper protrusions 24.

The disclosed example illustrates the inner surface 22 of the aperture 16 having an intermediate section or portion thereof devoid of or without protrusions between the upper protrusions 24 and the lower protrusions 26. Accordingly when viewed in cross-section, as illustrated in FIGS. 2-4, the aperture 16 illustrates an inner surface 22 having three zones or sections, an upper zone 60 including the upper protrusions 24, a lower zone 62 including the lower protrusions 26, and a middle zone 64 between the upper zone 60 and lower zone 62. The middle zone 64 having a width greater than that of the upper zone 60 or lower zone 62.

When viewed from the upper surface or in the direction of the longitudinal axis 20, the upper zone 60 has an inner diameter 66 established by the crests or ends 34 of the upper protrusions 24. The lower zone 62 has an inner diameter 68 established by the crests or ends 40 of the lower protrusions 26. The middle zone 64 has an inner diameter established by the inner surface 22 of the aperture 16. In the disclosed example, the inner diameter 70 of the middle zone 64 is greater than the inner diameters 66, 68 of the upper zone and lower zone 60, 62. Further, the inner diameter 66 of the upper zone 60 is greater and the inner diameter 68 of the lower zone 62.

In the disclosed example, the upper zone 60 is located adjacent the upper surface 14 and the lower zone 62 is located adjacent the lower surface 12. Such a configuration allows a reduction in the thickness, the distance between the upper surface 14 and lower surface 12 of the plate 10.

FIGS. 5-9 illustrate the fastener 18, for example a bone screw, for use with the bone plate 10. The fastener includes a head 82 and a shank 84. The head 82 having a generally conical shape and a double lead 94, 96 tapered thread 86. The leads are 180° opposite one another. In the present example, the head 82 has an 18° taper from the longitudinal or center axis 92 of the fastener 18, see FIG. 10. The shank 84 having a double lead thread 88 having a pitch equal to that of the thread 86 of the head 82 whereby the head 82 and shank 84 travel the same distance per rotation. In the disclosed example, the thread 86 of the head 82 has a thread or flank angle 98 of 105° resulting in a greater strength and torque transmission capability due to the increased thickness or width of the root or base of the thread. The increased flank angle provides increased space between respective or adjacent flanks 100, 102. The fastener or screw 18 further includes a non-threaded neck 90 between the head 82 and shank 84. A drive aperture or socket 104 suitable for receiving a driving tool (not shown) is in one end of the head 82.

Figure 11:
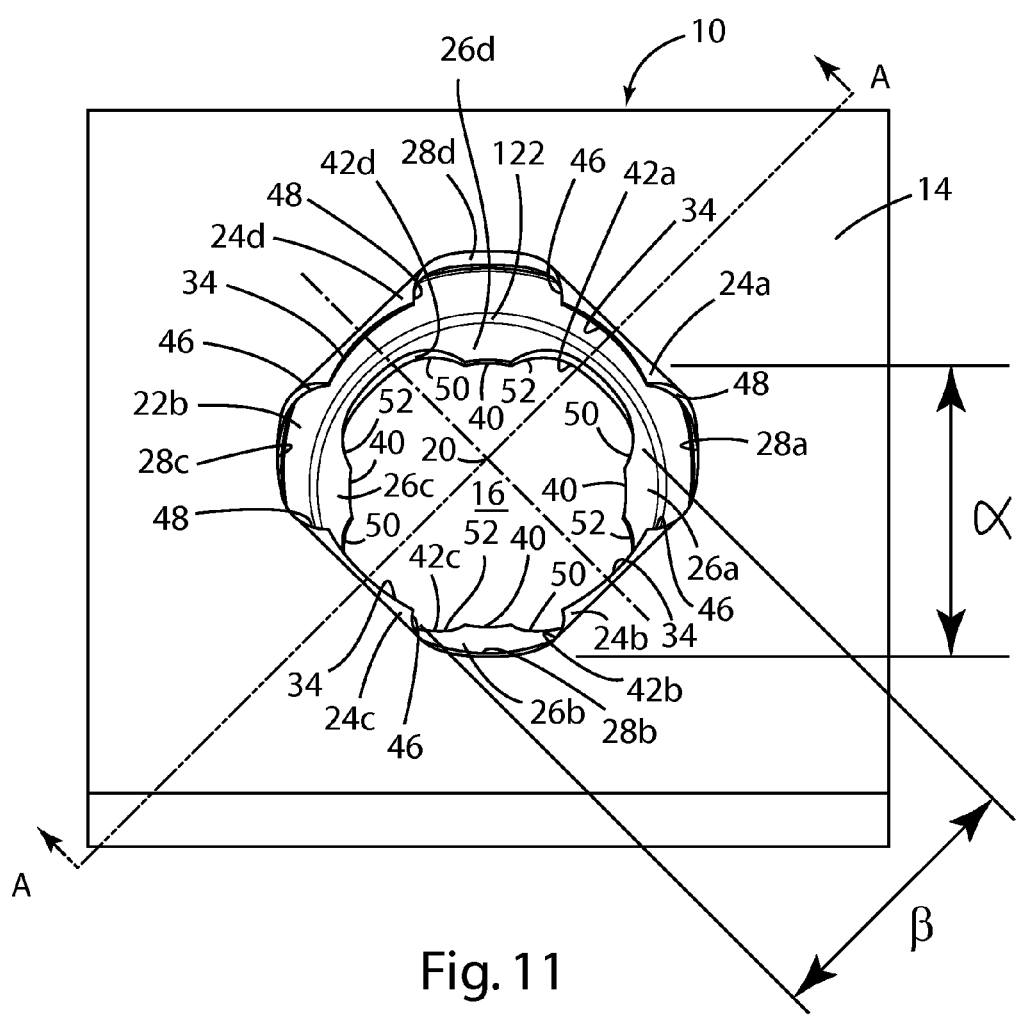
FIG. 11 is a partial perspective view of a bone plate having an aperture illustrating spacing between the respective projections and gaps.

As illustrated in FIG. 11 the aperture 16 the spacing or distance, when viewed along the longitudinal axis 20 of the aperture 16, between opposing upper gap 28 and lower protrusions 24 is the same as the spacing or distance between an adjacent set of opposing upper protrusions 26 and lower gaps 42 offset from the first set by 45°. For example, the lower projection 26b is offset 45° from the upper projection 24b and the upper gap 28b is offset from the lower gap 42c at 45°. As illustrated, the upper gap 28b is diametrically opposite the lower projection 26d. The planar spacing or distance α, when measured in a plane perpendicular to the longitudinal axis 20 of the aperture 16, between the upper gap 28b and lower projection 26d is the same as the planar spacing or distance β between the upper projection 24c and lower gap 42d. As illustrated, the planar spacing or distance between respective upper projections 26a-d and correspondingly opposing or opposite lower gaps 42a-d remains the same as does the distance between upper gaps 28a-d and correspondingly opposing or opposite lower projections 24a-d.

The aperture 16 according to the exemplary embodiment provides eight discrete angular positions, each providing the same angular insertion angle for the fastener 18. The embodiment may include additional gaps and lower protrusions or less gaps and protrusions as needed depending upon the thread configuration of the fastener and the retention force desired. The embodiment contemplates the use of between 3-5 sets of projections and gaps. In addition, the bone plate 10 may include multiple apertures 16 each having different configurations; i.e. different configurations of projections and gaps.

Figure 12:
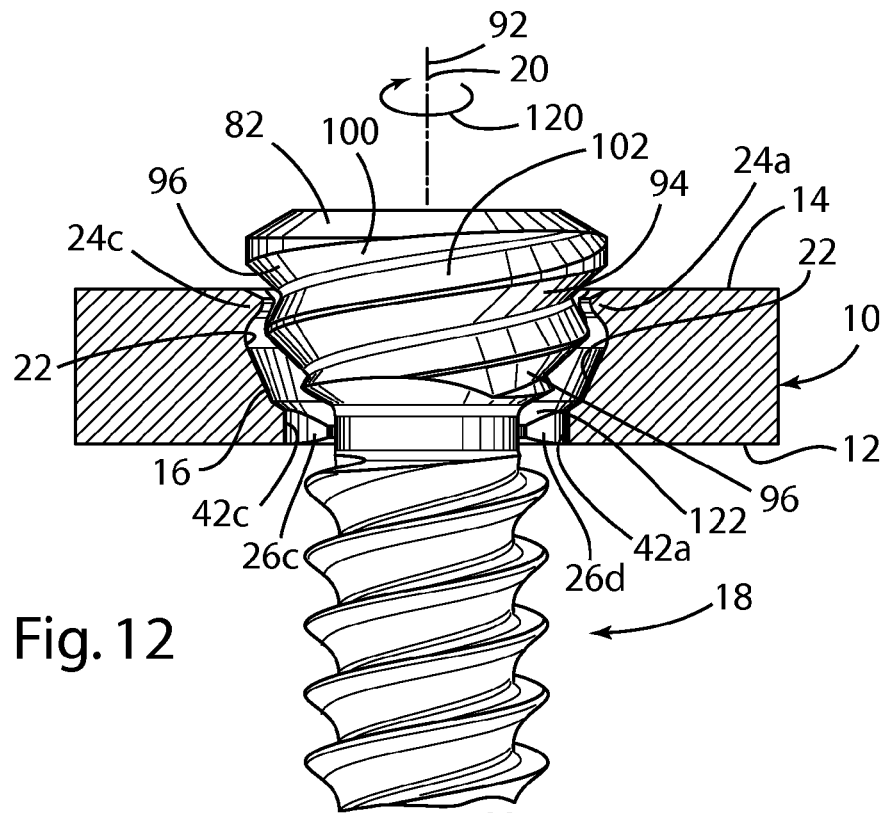
FIG. 12 is a partial cross-sectional view, taken along lines A-A of FIG. 11, illustrating the fixation element partially engaged in the aperture wherein the longitudinal axis of the fastener and aperture are coaxial.
Figure 13:
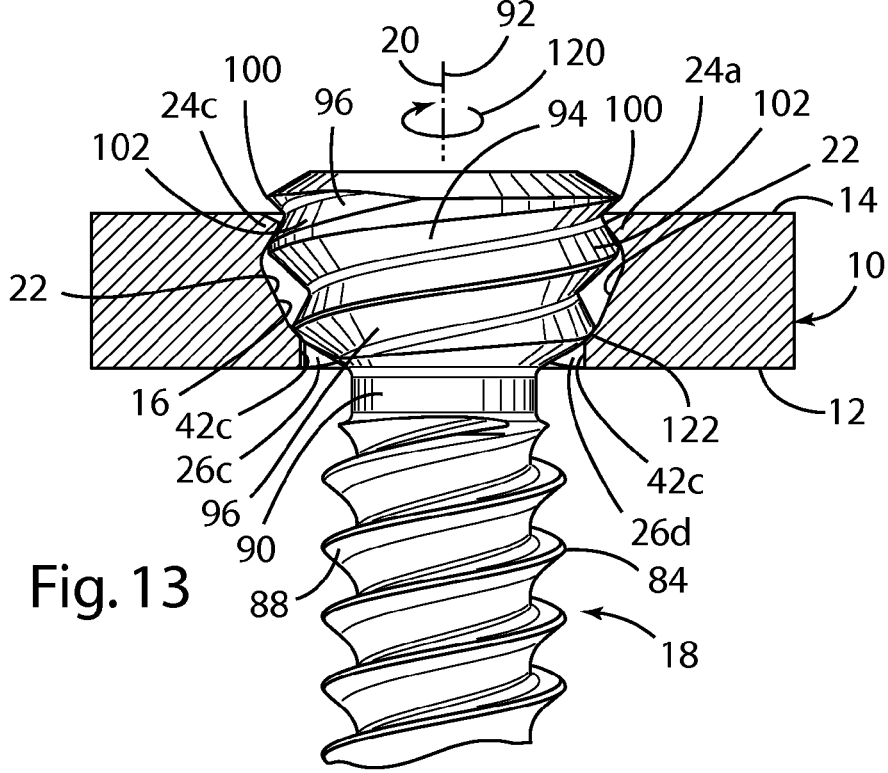
FIG. 13 is a partial cross-sectional view, taken along lines A-A of FIG. 11, illustrating the fixation element engaged and seated in the aperture wherein the longitudinal axis of the fastener and aperture are coaxial.

Turning to FIGS. 12-13 there is shown a fastener 18 inserted into an aperture 16 according to an exemplary embodiment of the invention. As illustrated, initially one of the double lead threads, here thread 94, engages a upper protrusion 24, identified as upper protrusion 24a in FIG. 11, while the opposite thread 96 engages the upper protrusion 24 located directly opposite or 180° apart, identified as upper protrusion 24c in FIG. 11. As the fastener 18 rotates in the direction illustrated by the arrow 120 initial contacting thread 94 engages the next or adjacent upper protrusion 24, identified as upper protrusion 24b in FIG. 11, while thread 96 engages the next upper protrusion 24, identified as upper protrusion 24d in FIG. 11.

Continued rotation of the fastener 18 drives the head 82 of the fastener 18 downwardly into the aperture 16 until the head 82 engages a seat 122 on or part of the inner surface 22 adjacent the lower protrusions 26. Engaging the seat 122 on the inner surface 22 provides a more stable locking surface and reduces the possibility of deflection of the lower projections 26 should the head 82 engage the lower projections 26; however, in certain situations it may be desirable for the head 82 to engage the lower projections 26.

When the fastener 18 is installed such that the longitudinal axis 20 of the aperture 16 coincides with the longitudinal axis 92 of the fastener 18, the outer or major diameter of the threads 88 of the shank 84 is sized to pass through the inner diameter 68 defined by the lower projections 26. In some instances, the outer or major diameter of the threads 88 of the shank 84 may exceed the inner diameter 68 in which case the threads 84 may engage the projections 26. The non-threaded neck 90 of the fastener 18 provides a clearance area whereby the fastener 18 may freely rotate without the threads 88 of the shank 84 engaging the lower projections 26. In the exemplary embodiment, the dimensional configurations of the thread pitch, and longitudinal distance to the seat 122 result in the head 82 reaching the seat 122 or bottoming out in one revolution of the initial contacting thread 94.

Figure 14:
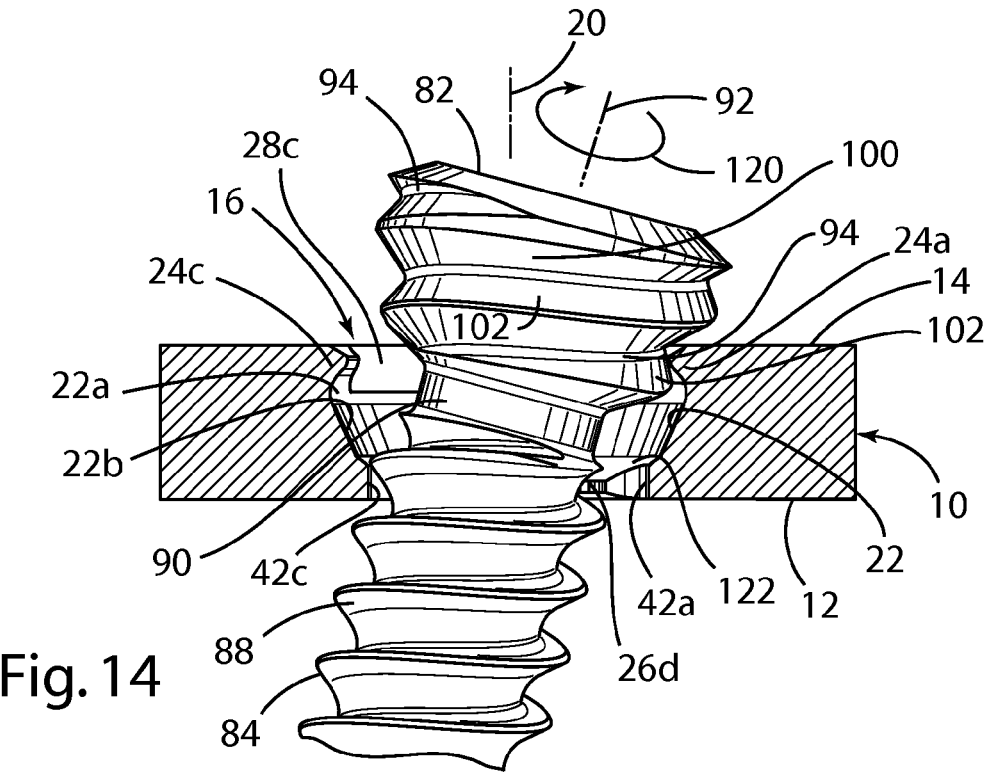
FIG. 14 is a partial cross-sectional view, taken along lines A-A of FIG. 11, illustrating the fixation element partially engaged in the aperture wherein the longitudinal axis of the fastener and aperture are offset with the longitudinal axis of the fastener placed at insertion angle.
Figure 15:
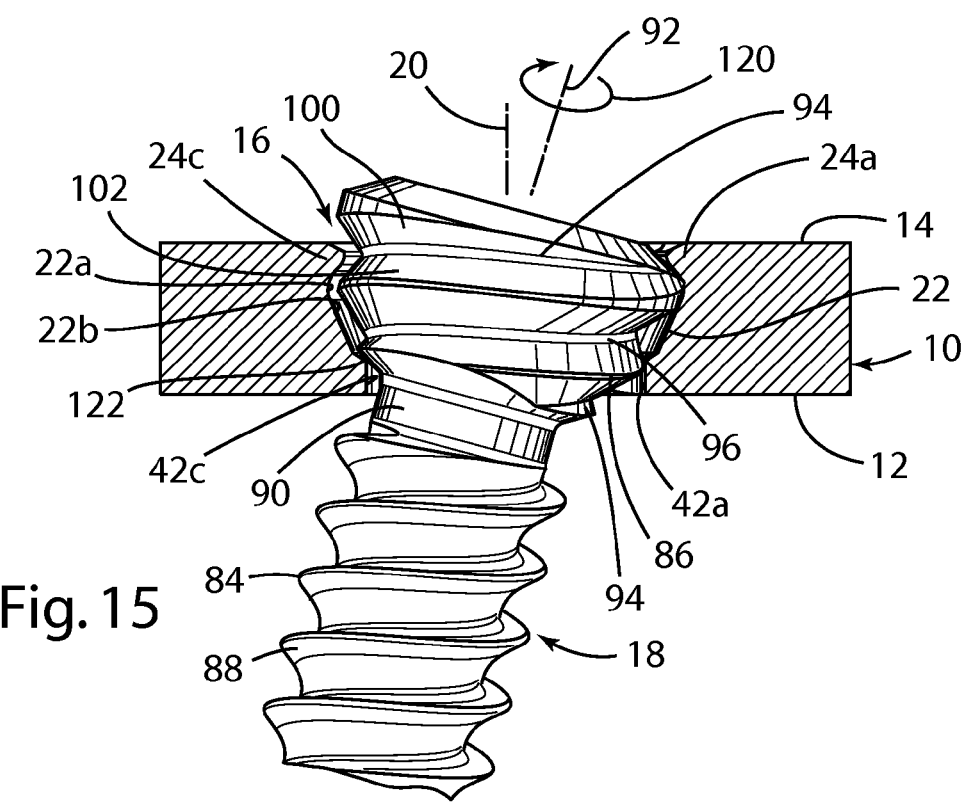
FIG. 15 is a partial cross-sectional view, taken along lines A-A of FIG. 11, illustrating the fixation element engaged and seated in the aperture wherein the longitudinal axis of the fastener and aperture are offset with the longitudinal axis of the fastener placed at insertion angle.

Turning to FIGS. 14-15 the fastener 18 is shown inserted into the aperture 16 at an angle of approximately 15° with respect to the longitudinal axis 20 of the aperture 16. As illustrated in FIG. 14, initially the thread 94 engages an upper protrusion 24, identified as upper protrusion 24a in FIG. 11, while the opposite thread 96 is spaced above and offset from the upper protrusion 24 located directly opposite or 180° apart, identified as upper protrusion 24c in FIG. 11. As illustrated, the outer portion of the thread 88 of the shank 84 is located adjacent the lower gap 42c. The gaps 42 sized such that the root diameter of the threaded portion 88 of the shank 84 is between and may contact the circumferential surface of the 42 or the sides 50, 52 of the lower protrusions 26.

Since the upper protrusions 24 are in a common plane, in the position in FIG. 14 the thread 94 would engage upper protrusion 24b, not shown due to the cross-sectional view. Continued rotation of the fastener 18 causes the thread 94 to engage upper protrusion 24c located directly opposite or 180° apart, from upper protrusion 24a. The insertion angle of the fastener 18 with the flank angle 98 of the threads 86 of the head 82 enable the thread 94 to engage three upper protrusions 24a, 24b, 24c. With the upper protrusion 24a near or contacting one flank 36 and the upper protrusion 24c near or contacting the opposing flank 38. As the thread 94 engages upper protrusion 24b the opposing thread 96 engages upper protrusion 24d. In the exemplary embodiment, when at an insertion angle of approximately 15°, three upper protrusions 24a, 24b, and 24c are contained in one thread 94 and the remaining upper protrusion 24d is contained in the opposite thread 96.

Similar to the example wherein the respective longitudinal axes of the aperture 16 and fastener 18 coincide, continued rotation of the fastener 18 causes the lower surface of the head 82 of the fastener 18 to contact the seat 122. As illustrated in FIG. 15 the lower gap 42*a* provides clearance for a portion of the threads 86 of the head 82 helping the head 82 contact and bottom out on the seat 122 rather than the lower protrusions 26. As illustrated, the conical shape of the inner surface 22 provides clearance for the head 82 when the fastener 18 is placed or inserted at an angle.

The disclosed example enables reduction in the overall thickness, that is distance between the upper surface 14 and lower surface 12 as the lower protrusions 26 and the gaps 42 adjacent the lower protrusions 26 provide both clearance and a guide for the shank 84 of the bone screw 80.

The description of the preferred embodiment is merely exemplary in nature and, thus, variations that do not depart from the gist of the invention are intended to be within the scope of the invention. Such variations are not to be regarded as a departure from the spirit and scope of the invention.

What is claimed is:

1. A bone fixation system comprising:
   a bone plate, said bone plate having an upper surface and a lower surface with an aperture extending between said upper surface and said lower surface;
   a plurality of upper protrusions, all of said upper protrusions spaced circumferentially in a common plane;
   a plurality of lower protrusions, all of said lower protrusions spaced circumferentially in a common plane, said lower protrusions out of phase with said upper protrusions.

2. The bone fixation system as set forth in claim 1 including said aperture having a longitudinal axis, said upper protrusions extending radially inward toward said longitudinal access; and
   said lower protrusions extending radially inward toward said longitudinal axis wherein said lower protrusions extend a greater distance radially inward then said upper protrusions.

3. The bone fixation system as set forth in claim 1 including a plurality of gaps between said upper protrusions, said gaps located in said common plane of said upper protrusions; and
   a plurality of gaps between said lower protrusions, said gaps located in said common plane of said lower protrusions wherein said gaps between said upper protrusions are located over said lower protrusions.

4. The bone fixation system of claim 1 including said aperture having first, second and third diameters, wherein said first diameter is less than said second diameter.

5. The bone fixation of claim 4 wherein said second diameter is greater than both said first diameter and said third diameter.

6. The bone fixation system of claim 4 wherein said first diameter is formed by said upper protrusions and said third diameter is formed by said lower protrusions.

7. The bone fixation system of claim 1 including a fastener, said fastener including a threaded head and a threaded shaft.

8. The bone fixation system of claim 7 wherein both said threaded head and said threaded shaft have double lead threads with both of said double lead threads having the same pitch.

9. The bone fixation system of claim 7 wherein at least one of either said upper protrusion or said lower protrusion engages at least one thread on said bone screw.

10. The bone fixation system of claim 7 wherein at least a portion of said threaded head has conical shape.

11. The bone fixation system of claim 10 wherein said conical angle is approximately 18° from a centerline of said fastener.

12. The bone fixation system of claim 7 wherein said threaded head has a plurality of threads, said threads having a thread angle of 90°-115°.

13. The bone fixation system of claim 12 wherein said threads have a thread angle of 105°.

14. The bone fixation system of claim 7 wherein said fastener has a non-threaded portion located between said threaded head and said threaded shank.

15. The bone fixation system of claim 7 wherein saki threaded head has a plurality of threads and said upper projections form an internal thread, said internal thread having a thread angle complementary to a thread angle of said threads of said threaded head of said fastener.

16. A bone plate comprising:
    an upper surface;
    a lower surface;
    an aperture extending between said upper and lower surface, said aperture having a longitudinal axis;
    said aperture having three sections, an upper section located closest to said upper surface, a lower section located closest to said lower surface, and a middle section located between said upper section and said lower section;
    said upper section including a plurality of protrusions extending radially inward toward said longitudinal axis, said lower section including a plurality of protrusions extending radially inward toward said longitudinal axis wherein said lower protrusions extend a greater distance radially inward than said upper protrusions, said middle section devoid of any protrusions extending radially inward toward said longitudinal axis;
    said aperture devoid of any protrusions extending radially inward toward said longitudinal axis between said protrusions in said upper section and said upper surface, said aperture devoid of any protrusions extending radially inward toward said longitudinal axis between said protrusions in lower section and said lower surface; and
    said lower protrusions out of phase with said upper protrusions.

17. A bone plate as set forth in claim 16 wherein said upper protrusions are spaced circumferentially in a common plane; and said lower protrusions are spaced circumferentially in a common plane.

18. A bone plate as set forth in claim 17 including a plurality of gaps between said upper protrusions, said gaps located in said common plane of said upper protrusions; and
    a plurality of gaps between said lower protrusions, said gaps located in said common plane of said lower protrusions when said gaps between said upper protrusions are located over said lower protrusions.

19. A bone plate as set forth in claim 16 wherein said upper section defines an upper diameter, said lower section defines a lower diameter, and said middle section defines a middle diameter wherein said upper diameter is less than said middle diameter and said lower diameter is less than said middle diameter and said upper diameter.

20. A bone plate as set forth in claim 16 wherein said middle section includes a seat surface.

* * * * *

UNITED STATES PATENT AND TRADEMARK OFFICE
CERTIFICATE OF CORRECTION

PATENT NO. : 9,987,062 B2  
APPLICATION NO. : 14/667390  
DATED : June 5, 2018  
INVENTOR(S) : Scott Epperly Page 1 of 1

It is certified that error appears in the above-identified patent and that said Letters Patent is hereby corrected as shown below:

In the Claims

Column 8, Line 14, please replace "saki" with --said--

Signed and Sealed this
Second Day of October, 2018

Andrei Iancu
*Director of the United States Patent and Trademark Office*